United States Patent [19]

Barnea

[11] 4,433,427
[45] Feb. 21, 1984

[54] METHOD AND APPARATUS FOR EXAMINING A BODY BY MEANS OF PENETRATING RADIATION SUCH AS X-RAYS

[75] Inventor: Daniel I. Barnea, Tel-Aviv, Israel

[73] Assignee: Elscint, Inc., Boston, Mass.

[21] Appl. No.: 342,732

[22] Filed: Jan. 26, 1982

[51] Int. Cl.³ .............................................. G03B 41/16
[52] U.S. Cl. ..................................... 378/146; 378/149
[58] Field of Search ................................ 378/146, 149

[56] References Cited

U.S. PATENT DOCUMENTS

| | | | |
|---|---|---|---|
| 2,730,566 | 1/1956 | Bartow | 378/146 |
| 4,114,041 | 9/1978 | Oliver | 250/445 T |
| 4,188,541 | 2/1980 | Hounsfield | 250/445 T |
| 4,234,794 | 11/1980 | Voinea | 378/146 |
| 4,366,574 | 12/1982 | Hill | 378/146 |

*Primary Examiner*—Craig E. Church
*Attorney, Agent, or Firm*—Sandler & Greenblum

[57] ABSTRACT

An image-reconstructive technique for examining a body by means of penetrating radiation, such as X-rays, is described in which a pre-body collimator having a two-dimensional array of radiation-transmitting holes each bordered by radiation non-transmitting walls is disposed between the body and the source of radiation, and a plurality of exposures are made onto a radiation-sensitive surface, in which the radiation is projected through the collimator while the radiation source is at a plurality of different locations, such that during the successive exposures, the radiation from the source passes through different ray paths defined by the holes in the pre-body collimator. The radiation level received by each of the radiation-sensitive surface elements is detected, stored, and processed to reconstruct the two-dimensional radiation pattern but with enhanced resolution. Preferably a post-body collimator is also used to suppress scattering. Described are a four-exposure procedure and a nine-exposure procedure.

24 Claims, 14 Drawing Figures

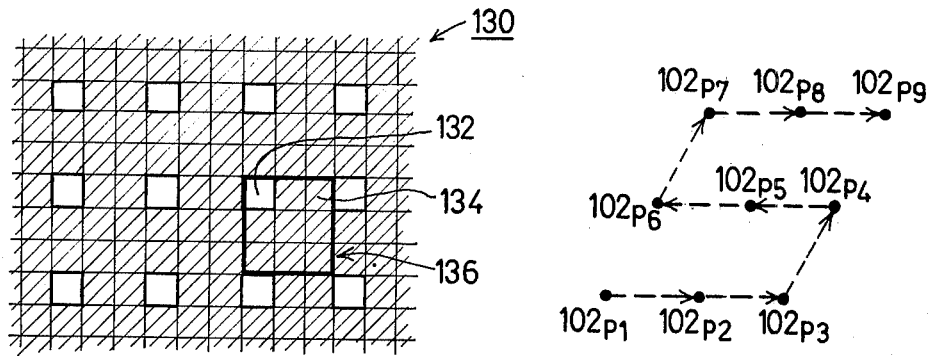
FIG.6
FIG 6a
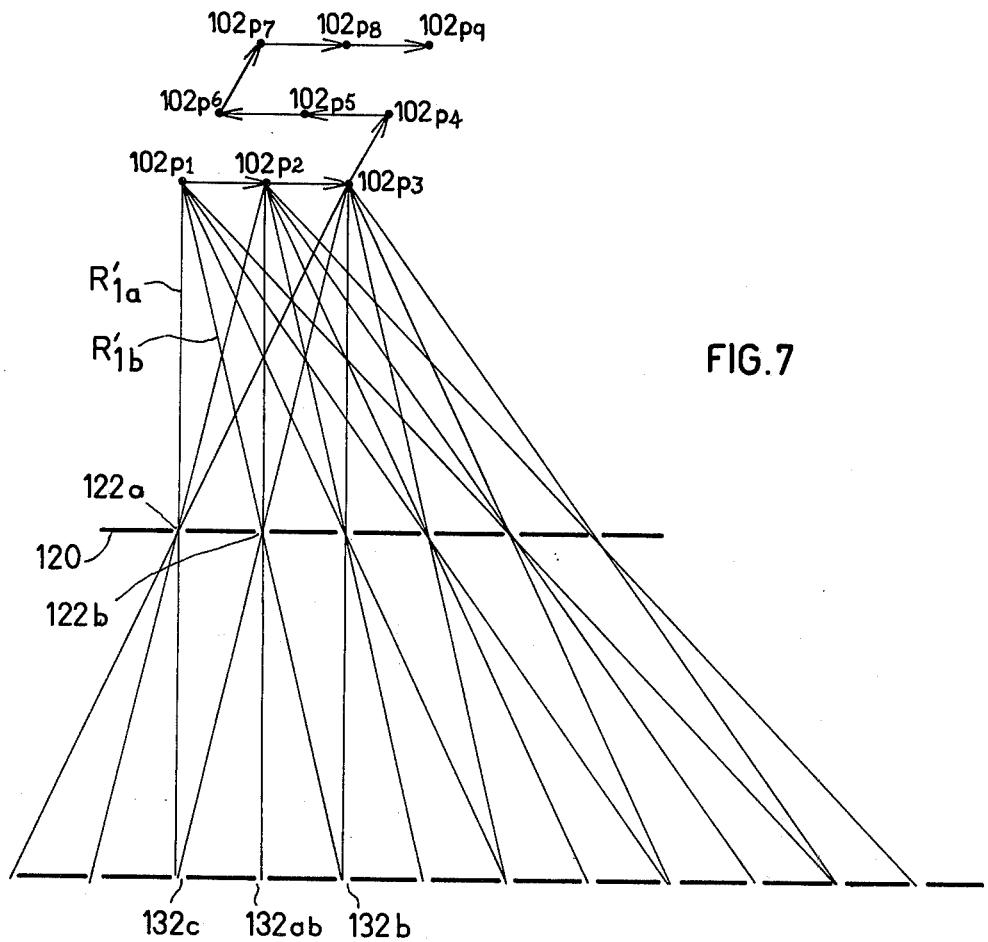
FIG.7

METHOD AND APPARATUS FOR EXAMINING A BODY BY MEANS OF PENETRATING RADIATION SUCH AS X-RAYS

BACKGROUND OF THE INVENTION

The present invention relates to a method and apparatus for examining a body by means of penetrating radiation. The invention is particularly useful in making medical examinations of a patient's body by X-rays, and is therefore described below with respect to such application, but it will be appreciated that the invention, or features thereof, could also be advantageously used in other applications, such as in medical examination procedures utilizing gamma rays, or in non-destructive industrial testing by X-rays or other penetrating radiation.

As distinguished from tomographic examinations, wherein a plurality of individual planar slices or sections of the examined body are imaged, the present invention is more particularly useful in single-view "full-body" examinations wherein the complete three-dimensional body, or a portion thereof, is imaged. In such "full-body" examinations, the complete three-dimensional body, or the portion thereof under examination, is exposed to the radiation (e.g., X-rays) projected from a source through the body onto a two-dimensional radiation-sensitive surface to produce a two-dimensional radiation pattern. Such a pattern is constituted of a plurality of picture elements, each of which is dependent on the attenuation suffered by the radiation traversing its respective substantially linear ray path through the examined body, from the radiation source to the point of impingement on the radiation-sensitive surface.

In using such single-view "full-body" X-ray imaging procedures for making medical examinations, it is highly desirable to maximize both the resolution and the stopping power of the radiation-sensitive surface. High resolution provides high definition of the image, thereby enabling the details to be better discerned, and high stopping power permits a larger proportion of the radiation passing through the object to be used, thereby minimizing the dosage required to be applied to the patient. Photographic film has been commonly used as the radiation-sensitive surface, but film has the disadvantages of poorly showing different densities and having very low stopping power. Because of these disadvantages, other detectors such as scintillating crystals, together with image-intensifier tubes and/or photographic film, have become more widely used as the radiation-sensitive surface. The stopping power of scintillating crystals is higher than film and increases with its thickness, but the resolution decreases with thickness. As a result, when a system is designed with thicker crystals in order to increase the stopping power and thereby to minimize the dosage to the patient, the resolution of the produced image suffers. This limits the extent to which the thickness, and thereby the stopping power, of the crystals can be increased.

An object of the present invention is to provide a method and apparatus for examining a body having advantages in the above respects. More particularly, an object of the present invention is to provide an examining method and apparatus in which the resolution of the produced image may be very substantially enhanced, thereby permitting the use of scintillating crystals having high stopping power so that both good resolution of the image and low dosage to the patient are more easily obtainable.

BRIEF SUMMARY OF THE INVENTION

According to a broad aspect of the present invention, there is provided a method and apparatus for examining a body by means of penetrating radiation projected through the body onto a two-dimensional radiation-sensitive surface to produce a two-dimensional pattern of the radiation absorbed by the body; characterized in that a pre-body collimator having a two-dimensional array of radiation-transmitting holes, each bordered by radiation non-transmitting walls, is disposed between the body and the source of radiation; and a plurality of successive exposures of the body is effected by projecting the radiation through the collimator and the body during a plurality of successive exposure periods in each of which the radiation source is at a different location with respect to the collimator, such that, during the different exposure periods, each element of the radiation-sensitive surface receives the radiation passing through the examined body via different ray paths defined by different holes in the collimator. The radiation level received by the radiation-sensitive surface elements during each of these exposures is detected, stored, and processed to reconstruct the two-dimensional radiation pattern, but with enhanced resolution.

The relative displacement between the radiation source and the collimator could be effected by displacing the collimator, but preferably is effected by displacing the radiation source. When the radiation source is an X-ray tube, as in the case of the preferred embodiments described below, the radiation source can be displaced by deflecting the electron beam of the X-ray tube across its target, or by displacing the X-ray tube itself.

It will thus be seen that the technique of the present invention is an image-reconstructive technique in which the capabilities of computers may also be exploited, as in computer-aided tomography (CAT), in order to reconstruct the image of the object being examined. However, in the present invention the reconstruction aided by a computer is of the "full body" being examined, i.e., the full body, or the portion thereof under examination, is exposed and imaged in two dimensions in order to obtain a single image with enhanced resolution and minimum patient dosage, as distinguished from the "reconstructive tomographic technique" in which planar slices or sections of the examined body are scanned from many angles and are reconstructed with the aid of a computer in order to produce a plurality of images relating to various sections or layers of the examined body without interference from other sections or layers.

Very significantly improved results are obtainable with the method and apparatus of the present invention by the addition of a post-body collimator disposed between the radiation source and the examined body in proper relationship to the prebody collimator. The post-body collimator also includes a two-dimensional array of radiation-transmitting holes each bordered by a radiation non-transmitting wall so dimensioned and arrayed with respect to those of the pre-body collimator such that the radiations passing through the same hole in the post-body collimator to the underlying radiation-sensitive surface element during the successive exposures, pass through different holes in the pre-body collimator during the successive exposures. Thus, the pre-body collimator shields the patient from substantially all the radiations except those which are useful to produce the resulting image on the radiation-sensitive surface, and the post-body colimator reduces the effects of scattering.

For purposes of example, the radiation source may be located during the successive exposures at two different positions along each orthogonal axis, i.e. at four different positions total, so that in a four-exposure examination procedure each radiation-sensitive surface element receives the radiation passing along four contiguous ray paths through the body being examined. This enhances the resolution by about a factor of two. The resolution may be further enhanced by providing a larger number of exposures in an examination procedure. For example, a nine-exposure procedure may be provided in which the radiation source is located at three different positions along each orthogonal axis, or nine positions total, whereupon each radiation-sensitive element would receive the radiation passing along nine contiguous ray paths through the body; such a nine-exposure procedure enhances the resolution by about a factor of three.

A further important advantage in using a nine-exposure procedure is that the holes in the pre-body collimator can be made substantially larger, thereby decreasing manufacturing costs. A still further advantage is that the holes in a nine-exposure procedure can be arranged such that in each exposure, certain holes receive direct radiation and others do not, thereby enabling the holes not receiving direct radiation to be used in determining radiation scatter, as will be described more particularly below.

Preferably, the radiation-sensitive surface is constituted of scintillating detectors optically coupled to an image intensifier tube forming an image on a TV or vidicon photoconductive surface, which surface is scanned by an electron beam to detect the radiation levels received by each of the radiation-sensitive surface elements. The output of the vidicon may be fed to an analog-to-digital converter and processed in a digital computer. The computer stores in a memory the information concerning the radiation levels received by each of the radiation-sensitive surface elements during each of the exposure periods and reconstructs the original two-dimensional radiation pattern, but with enhanced resolution over that obtainable in the conventional procedure. The reconstructed pattern may then be displayed, or stored for later display or for further processing.

Further features and advantages of the invention will be apparent from the description below.

BRIEF DESCRIPTION OF THE DRAWINGS

The invention is herein described, by way of example only, with reference to the accompanying drawings, wherein:

FIGS. 6 and 6a are diagrams corresponding to FIGS. 4 and 4a, respectively, for a nine-exposure procedure; and FIG. 7 is a ray-path diagram helpful in understanding the operation, and the advantages, of a nine-exposure procedure using collimators constructed as illustrated in FIGS. 6 and 6a.

DESCRIPTION OF PREFERRED EMBODIMENTS

General Construction

Figure 1:
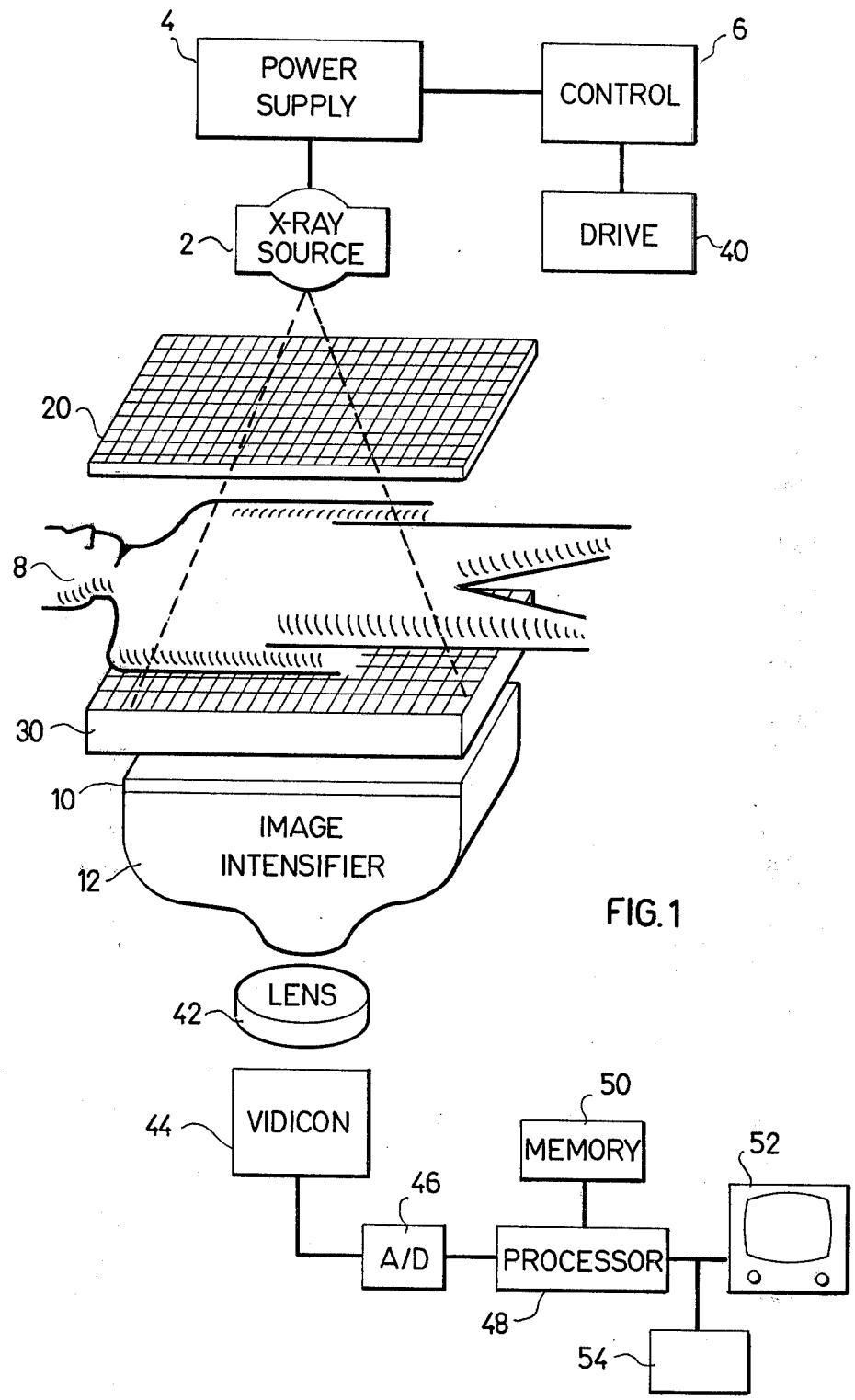
FIG. 1 is a schematic block diagram illustrating one form of apparatus constructed in accordance with the present invention.

FIG. 1 of the drawings illustrates the overall arrangement of one form of apparatus which may be used for examining bodies according to different plural-exposure procedures in accordance with the present invention. For purposes of example, the use of such apparatus is described below for examining bodies in accordance with a four-exposure procedure and also in accordance with a nine-exposure procedure, but it will be appreciated that such apparatus could also be used in other plural-exposure procedures in accordance with the invention.

The apparatus illustrated in FIG. 1 includes a radiation source 2, such as an X-ray tube, energized by a power supply 4 under the control of a control unit 6 to project X-rays through an object 8 onto a radiation-sensitive surface 10. The latter surface is constituted by a two-dimensional array of scintillation detectors optically coupled to an image intensifier 12. The X-rays projected by tube 2 penetrate the object 8 and are partially absorbed according to the X-ray absorption characteristic of the object along each line, or ray path, of the X-rays from the tube 2 to the point of impingement on the scintillation detectors 10. A two-dimensional radiation pattern is thus produced on the detectors 10. This pattern is constituted of a plurality of picture elements, each of which is dependent on the attenuation suffered by the radiation when traversing the respective line or ray path through the object from the source to the respective detector element.

Figure 2:
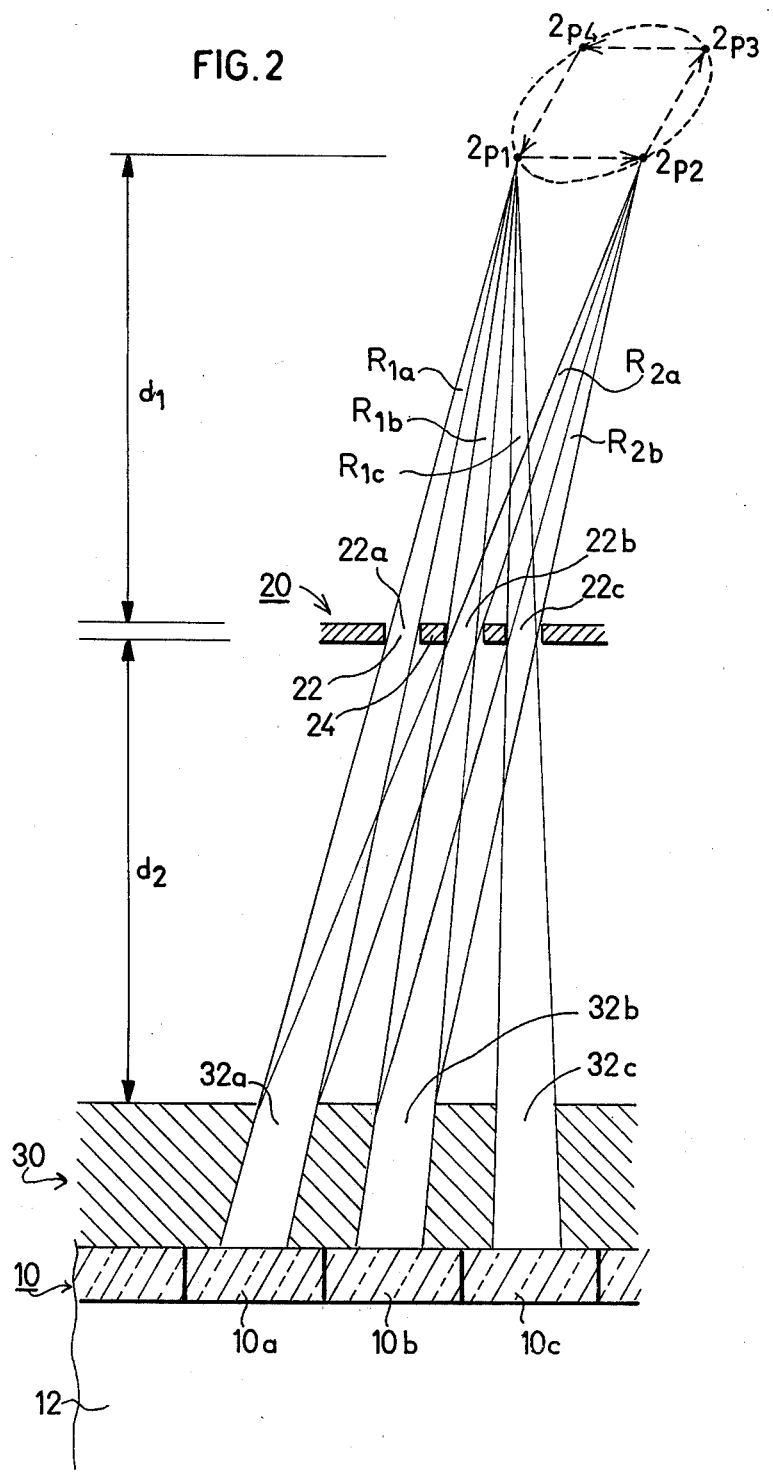
FIG. 2 is a ray-path diagram helpful in understanding the present invention.

The system illustrated in FIG. 1 further includes a pre-body collimator 20 located between the X-ray source 2 and the body 8 being examined, and a post-body collimator 30 disposed between the body 8 and the scintillation detectors 10. With reference to the post-body collimator 20 particularly illustrated in FIGS. 2-4, it will be seen that it includes a two-dimensional array of radiation-transmitting holes 32 each bordered by radiation non-transmitting walls 34. As shown in FIG. 2, the pre-body collimator 20 has a corresponding array of radiation-transmitting holes 22 each bordered by a radiation non-transmitting wall 24, except that the dimensions of holes 22 in collimator 20 are smaller than the dimensions of holes 32 in collimator 30, as will be described more particularly below. In addition, the thickness or height of the pre-body collimator 20 is considerably less than that of the post-body collimator 30, the latter collimator having a substantial thickness ("H", FIGS. 3, 3a) because of its scatter-suppressing function. Thus, the post-body collimator 30 should have an aspect ratio (e.g., 8:1) consistent with the scatter reduction desired.

Tube 2 provides substantially a point source of X-rays, which rays fan out in two dimensions as they progress through the body 8 being examined, to impinge on a two-dimensional scintillation detector 10. Accordingly, the holes 22 in the pre-body collimator 20, and the holes 32 in the post-body collimator 30, are all oriented along the radial lines from the point source 2 to the scintillation detector 10. The scintillation detector 10 would normally be a single crystal directly underlying the post-body collimator 30 for receiving the radiation passing through the holes of the respective collimator.

The system illustrated in FIG. 1 further includes a drive, generally designated 40, for displacing the point source of X-rays 2 along both the X-coordinate and the Y-coordinate with respect to the two collimators 20, 30, the body 8 being examined, and the scintillation detector 10. For this purpose, drive 40 effecting the displacement may either be a mechanical drive which displaces the complete X-ray tube 2, or may be an electrical drive which displaces the electron beam within the X-ray tube 2 so as to impinge a different portion of the tube target.

In examining the body 8 by means of the X-rays projected through the body from the X-ray source 2 onto the scintillation detector 10, the body 8 is exposed to the radiations during a plurality of successive exposure periods in each of which the radiation source 2 is at a slightly different location with respect to the collimators 20 and 30, and the examined body. The arrangement is such that during the successive exposures the radiation from source 2 passes through different ray paths defined by different holes in the pre-body collimator 20, but by the same holes in the post-body collimator 30, before impinging on the scintillation detector 10.

The scintillation detector 10 converts the pattern of radiation impinging thereon to a pattern of photons, which pattern is intensified by image intensifier 12 and projected, via a lens 42, onto the photoconductive surface of a TV or vidicon tube 44. The vidicon tube 44 is scanned by an electron beam to detect the intensity of the radiation impinging on each element of the scintillation detector 10. The intensity level of each such element is converted to digital form by an analog-to-digital converter 46, and the digital information is fed to a digital processor 48 having a memory 50 in which the information is stored for the time being.

Before making the next exposure, the radiation source 2 is moved with respect to the two collimators 20, 30 and the examined body 8, to a new location, whereupon the next exposure is made. The radiation level received by each element of the scintillation detector 10 during the second exposure is processed in the same manner as above with respect to the first exposure, and stored in the memory 50. The foregoing procedure is repeated for a third and a fourth exposure.

After the four exposures have been completed, memory 50 includes the information as to the radiation levels detected by each element of the scintillation detector 10, corresponding to the attenuation suffered by the radiation when traversing the different ray paths (defined by the different holes of the pre-body collimator 20) during the different exposures and impinging the same element of the detector (defined by the overlying hole of the post-body collimator 30). Since all the required parameters are known with respect to the information stored in memory 50 for each element of the detector during the four exposure periods, this information may be used by the processor 48 for reconstructing a single two-dimensional radiation pattern, but with enhanced resolution. This pattern may then be displayed in the display unit 52, or stored on tape in tape unit 54 for later display or further processing.

Example of a Four-Exposure Procedure

The following describes a four-exposure procedure, during which the X-ray source 2 is located at the four different positions, schematically designated $2_{P1}$, $2_{P2}$, $2_{P3}$, and $2_{P4}$ in FIG. 2. It will be seen that in these four positions, the X-ray point source 2 traces a square so as to assume two different positions along the X-coordinate and two different positions along the Y-coordinate, or a total of four different positions. In practice, the point source 2 could be displaced to trace a circle, and energized when located at each of the above four different positions. During this movement of the X-ray point source 2, the remainder of the system, i.e., the two collimators 20, 30, the body 8 being examined, and the scintillation detector 10, all remain stationary.

Figure 3:
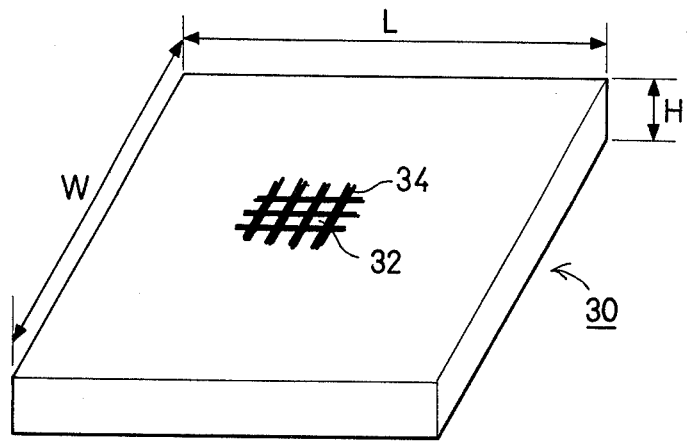
FIG. 3 is a three-dimensional view illustrating the construction of the collimators in FIG. 1.
Figure 3A:
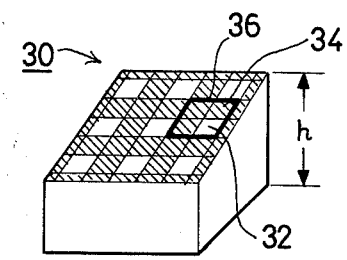
FIG. 3a is an enlarged fragmentary view thereof, particularly of the post-body collimator to suppress scattering.

The four-exposure procedure illustrated in FIG. 2 is for use with the construction illustrated in FIGS. 3, 3a for the two collimators 20 and 30. The collimator illustrated in FIGS. 3 and 3a is the post-body collimator 30, having an overall length, width and thickness or height indicated at L, W, and H, respectively. Its holes 32 are of square configuration, having a width (w) and length (l) equal to each other, and also equal to the wall 34 thickness "t" between holes (w=l=t), so that the holes 32 constitute one-fourth the cross-sectional area of the respective element 36 of the collimator. The thickness or height (H) of collimator 30 is sufficient so as to provide the appropriate aspect ratio (e.g., 8:1) consistent with the degree of scatter-reduction desired to be provided by the collimator.

It will be appreciated that, in FIG. 2, the movement of the source 2 relative to its spacing from the two collimators 20 and 30 (i.e. dimensions $d_1$ and $d_1+d_2$, respectively) is considerably exaggerated, for purposes of clarity, such that the displaced beams would appear to be partially blocked by the post-body collimator 30. In actual practice, this effect would be extremely small and could be compensated for according to known techniques.

The construction of the pre-body collimator 20 is the same as the post-body collimator 30, except that the thickness of the pre-body collimator 20 is substantially less (e.g., see FIG. 2), since it does not have the anti-scattering function of collimator 30, but need only be sufficiently thick to block the passage of the X-rays; also, the dimensions of the holes 22 are smaller than the holes 32 in collimator 30. The dimensions of the holes 22 in collimator 20 depend on its spacing from the X-ray source 2 compared to the spacing of the post-body collimator 30 to the X-ray source 2. Thus, if the pre-body collimator 20 is mid-way between the x-ray source 2 and the post-body collimator 30 (i.e., $d_1=d_2$ in FIG. 2), its openings 22 would be one-half the size of openings 32 in the post-body collimator 30. The relative dimensions of the openings 22 with respect to the bordering walls 24 would be the same as in the post-body collimator 30 (i.e., w=l=t) so that also in the pre-body collimator 20, the total cross-section of the holes (e.g. 22) constitutes one-fourth of the total cross-section of the collimator grid surface. Thus, the walls 24 bordering the holes in the pre-body collimator 20 block three-fourths of the radiation from the body during each of the four exposure periods, so that the body will be exposed, during all four exposure periods, to approximately the same total radiation to which it would be exposed in one exposure (for a lower-resolution image) without the pre-body collimator 20.

Figure 4:
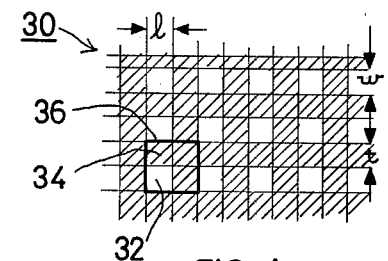
FIG. 4 is a diagrammatical view illustrating the construction of the FIG. 3 collimators for use in a four-exposure procedure.
Figure 4A:
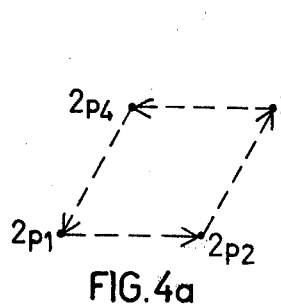
FIG. 4a is a diagram illustrating the four different positions of the radiation source in the four-exposure procedure.

The four-exposure procedure diagrammatically illustrated in FIG. 2, using the collimator construction of FIG. 4 and the point-source 2 positioning of FIG. 4a, is as follows:

At the first position $2_{P1}$ of the X-ray source 2, the rays are projected through the body 8 being examined along a plurality of ray paths, e.g. $R_{1a}$, $R_{1b}$, $R_{1c}$. It will be seen that ray path $R_{1a}$ passes through hole 22a of the pre-body collimator 20 and the aligned hole 32a of the post-body collimator 30; ray path $R_{1b}$ passes through hole 22b of collimator 20 and the corresponding aligned hole 32b of collimator 30; and ray path $R_{1c}$ passes through hole 22c of collimator 20 and corresponding aligned hole 32c of collimator 30.

Accordingly, during this first exposure period when the X-ray source is at its first position $2_{P1}$, the elements or portions of the scintillation detector $10_a$, $10_b$, $10_c$... underlying holes 32a, 32b, 32c, ... of the post body collimator 30 receive the X-ray radiations passing along their respective ray paths $R_{1a}$, $R_{1b}$, $R_{1c}$..., through the body 8 located between the two collimators 20 and 30.

The scintillation detector 10 is optically coupled to the underlying image intensifier 12, so that the two-dimensional radiation pattern passing through the holes 32 of collimator 30 onto the underlying elements of the scintillation detector 10 will be imaged on the face of the image intensifier 12. This image is projected via lens 42 (FIG. 1) onto the photoconductive surface of vidicon tube 44 and is scanned by an electron beam to detect the intensity of the radiations impinging each of the above elements of the scintillation detector 10. This intensity level is converted to digital form by analog-to-digital converter 46, and the digital information is fed to digital processor 48 and is temporarily stored in its memory 50.

The point source 2 of X-rays is then moved to the second position $2_{P2}$ illustrated in FIG. 2, while the two collimators 20, 30, as well as the body 8 being examined and the remainder of the system illustrated in FIG. 1, are retained stationary in their previous positions. In this second position $2_{P2}$, the X-rays emitted from the source now pass through the examined body 8 along slightly different ray paths, these being designated $R_{2a}$, $R_{2b}$, etc.

As shown in FIG. 2, the geometry of the system is such that the radiation passing along ray path $R_{2a}$ in this second exposure impinges upon its respective scintillation detector element $10_a$ underlying the corresponding hole 32a of the post-body collimator 30, but does not pass through hole 22a of the pre-body collimator 20 (hole 22a corresponding to and aligned with hole 32a of the post-body collimator 30 during the first exposure period); rather, the radiation passes through the next adjacent hole 22b of the pre-body collimator 20. In a similar manner, the radiation impinging upon scintillation detector element $10_b$ underlying hole 32b of the post-body collimator 30 passes through the next adjacent hole 22c of the pre-body collimator 20, and so on with the other elements of the detector 10.

Thus, during this second exposure when the point source 2 of X-rays is now in position $2_{P2}$ in FIG. 2, each point of the radiation pattern imaged on the elements of the scintillation detector 10 represents the radiation passing along a slightly different, but adjacent, ray path through the examined body 8 than during the first exposure when source 2 was at position $2_{P1}$. This radiation pattern, after being scanned in the vidicon 44 and processed in the analog-to-digital converter 46 and digital processor 48, is also stored in the memory 50.

The X-ray point source 2 is then moved to the third position $2_{P3}$ in FIG. 2, namely, a distance equal to that between its first two positions $2_{P1}$ and $2_{P2}$ but along the Y-axis. The body 8 is then subjected to a third exposure during which the radiations passing through the holes 32 in the post-body collimator 30 to the underlying elements of the scintillation detector 10, again travel along slightly different ray paths, namely, through the next contiguous openings 22 of the pre-body collimator 20 along the Y-coordinate. This radiation pattern is also scanned in the vidicon 44 and stored in the memory 50 after being processed by the analog-to-digital converter 46 and digital processor 48.

The X-ray point source 2 is then moved to the fourth position $2_{P4}$ illustrated in FIG. 2, and the examined body 8 is subjected to a fourth exposure, during which the radiations passing through the post-body collimator holes 32 to the underlying detectors 10 again travel along slightly different ray paths through the next contiguous openings 22 of the pre-body collimator 20, this radiation pattern also being scanned in the vidicon 44 and stored in the memory 50.

With the fourth exposure, the examination of body 8 is completed, and the X-ray point source 2 is returned to its initial position $2_{P1}$ in preparation for examining another body.

It will be seen that, as a result of subjecting the examined body 8 to the four above-described exposures, the memory 50 has now stored in it the radiation levels detected by each element of the detector 10 during each of the four exposures. As will be recalled, each element of detector 10 receives, during all four exposures, the radiation passing through the same hole 32 in the post-body collimator 30 but through a different hole 22 in the pre-body collimator 20 defining a different ray path through the examined body 8. Since the parameters of the system, including the position of the point source during each of the four exposures, the spacing between the pre-body collimator 20, the examined body 8, and the post-body collimator 30, as well as the dimensions of the holes and walls in the two collimators, are all known, the computer may make the necessary computations in order to reconstruct the two-dimensional radiation pattern detected during the four exposures into a single, two-dimensional, enhanced-resolution radiation pattern.

Figure 5A:
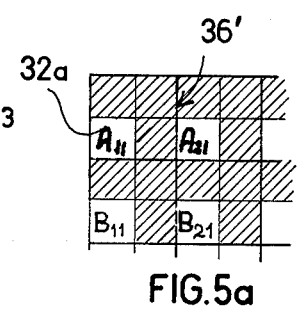
FIGS. 5a-5e are diagrams illustrating the manner of reconstructing the final two-dimensional radiation pattern from the information obtained and stored during each of the exposures in a four-exposure procedure.
Figure 5B:
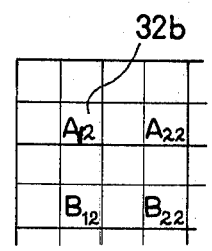
Figure 5C:
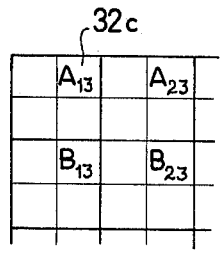
Figure 5D:
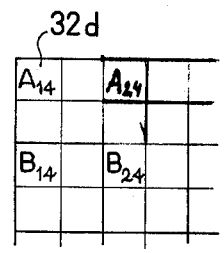
Figure 5E:
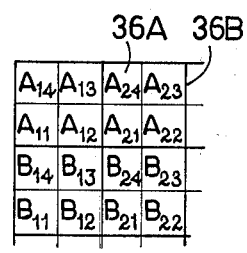

FIGS. 5a–5e illustrate the manner of using the information detected during the four exposures (FIGS. 5a–5d) for reconstructing the single enhanced-resolution radiation pattern (FIG. 5e).

Thus, as shown in FIG. 5a, during the first exposure, when the radiation source 2 is at position $2_{P1}$, there is detected and stored only the radiation passing through holes 32, which constitutes one-fourth of the respective image area corresponding to element 36 of the post-body collimator 30 as illustrated in FIGS. 3a and 4. The latter area is indicated as 36′ in FIG. 5a, wherein it will be seen that only one-fourth of each of such areas indicated by sub-element 32a, receives radiation during the first exposure, these radiation-receiving areas being indicated by the sub-elements $A_{11}$, $A_{21}$ in the first horizontal row, and $B_{11}$, $B_{21}$ in the second horizontal row.

During the second exposure when the radiation source 2 is at position $2_{P2}$, again only one-fourth of the surface area of each of the respective image elements 36' detects the radiation, such surface area sub-elements being designated 32b in FIG. 5b. Similarly, during the third exposure when the point source 2 is at position $2_{P3}$, again only one-fourth of the area of each image element 36' detects the radiation, as illustrated by sub-element 32c in FIG. 5c; and likewise during the fourth exposure, only the remaining one-fourth area of each image element 36' detects the radiation as illustrated by sub-element 32d in FIG. 5d.

All the foregoing information stored within the memory 50 of the processor 48 during the four exposures, together with the above-mentioned known parameters, is processed so as to reconstruct the two-dimensional radiation pattern, as illustrated in FIG. 5e, wherein each image element, therein designated $36_A$, $36_B$, etc. corresponding to the surface areas 36 of the post-body collimator 30 as illustrated in FIGS. 3a and 4, is constituted of the four sub-elements 32a–32d corresponding to the four detected levels of radiation passing through the corresponding post-body collimator hole 32 during the for exposures. Thus, the reconstructed image as illustrated in FIG. 5e is derived from the information obtained during the four exposures in each of which the radiation passes through the examined body along a slightly different path, and is therefore of enhanced resolution as compared to images produced by the conventional single-exposure procedure.

In the example illustrated in FIG. 2, the distance ($d_1$) between the pre-body collimator 20 and the point source 2 is equal to the distance ($d_2$) between the post-body collimator 30 and the point source 2. In such a case, the size of the holes 22 in the pre-body collimator 20 should be one-half that of the holes 32 in the post-body collimator. Also, the displacement distance of the point source, from one position to the next, should be twice the size of the holes in the post-body collimator 30. For example, the size of hole 32 could be 0.2 mm (i.e. $l=w=0.2$ mm), that of hole 22 could be 0.1 mm, and the spacing between point source positions could be 0.4 mm. Such an arrangement would produce the results illustrated in FIG. 2 and would provide a resolution enhanced by about a factor of two over a conventional system.

Example of a Nine-Exposure Procedure

A further increase in enhancement of the image resolution may be obtained by increasing the number of exposures to which the examined body is subjected, with a corresponding decrease in the amount of radiation to which the body is exposed during each such exposure. For purposes of example, a nine-exposure procedure is illustrated in FIGS. 6, 6a and 7, such a procedure not only providing further enhanced resolution, but also other advantages as will be described more particularly below.

For a nine-exposure procedure, the post-body collimator would be constructed as illustrated in FIG. 6, the collimator therein being designated 130, and the point source of radiation would be located at the nine different positions indicated at $102_{P1}$ ... $102_{P9}$ in FIG. 6a. FIG. 7, which diagrammatically illustrates some of the ray paths during such a nine-exposure procedure, will be helpful in understanding the operation of the system.

Thus, as shown particularly in FIG. 6, the post-body collimator 130 is provided with holes 132 having a cross-sectional area constituting only one-ninth of the cross-sectional area of the reconstructed image element 136. That is to say, the walls 134 of each image element would have a thickness twice the dimensions of holes 132, so that the holes 132 constitute one-ninth of the surface area of the two collimator grid. The remaining eight-ninths of the surface area of the two grids is constituted of the bordering walls 134. Accordingly, the examined body would be subjected to one-ninth of the total radiation during each exposure, for a total of nine exposures. In each exposure the point source is moved to one of three different positions along each of the two axes, as illustrated in FIGS. 6a and 7.

Actually, the nine-exposure procedure and collimator construction are very similar to the above-described four-exposure procedure and collimator construction, with the addition of a further hole in the collimator intermediate each two holes along each axis (thereby providing three holes along each axis, or a total of nine holes) and with the further addition of an exposure location intermediate each two exposure locations (thereby providing three exposure locations along each axis, or a total of nine exposure locations). This will be more readily apparent from the diagram in FIG. 7, wherein holes 132a and 132b in the post-body collimator 130 correspond to holes 32a and 32b in the corresponding collimator 30 used in the four-exposure procedure, as illustrated in FIG. 2. In the nine-exposure procedure of FIG. 7, an intermediate hole 132ab is provided exactly mid-way between holes 132a and 132b along both the X-axis and Y-axis, so that a complete image element, designated 136 in FIG. 6 (corresponding to image element $36_A$, $36_B$, etc. in FIGS. 5a–5e) is now constituted of nine sub-elements, rather than of four sub-elements (32a–32d) in the above-described four-exposure procedure.

As also indicated above, in the nine-exposure procedure the radiation source is moved to an additional mid-way location between each pair of positions along each axis in the four-exposure procedure, resulting in a total of nine different positions. This mid-way position is illustrated along the X-axis in FIG. 7 as position $102_{P2}$, which is exactly mid-way between its positions $102_{P1}$ and $102_{P3}$, it being appreciated that there are corresponding mid-way positions also along the Y-axis, e.g., as indicated by the fourth position $102_{P4}$ in FIG. 7.

Now, when the radiation source is at the first position $102_{P1}$ in FIG. 7, it will be seen that the radiation will pass along a first ray path $R'_{1a}$ through hole 122a of collimator 120 and hole 132a of collimator 130, and along a second ray path $R'_{1b}$ through hole 122b of collimator 120 and through hole 132b of collimator 130. In other words, the mid-way hole 132ab in the post-body collimator 130 will not receive any direct radiation during this first exposure when the radiation source is at position $102_{P1}$.

If the radiation source would be moved directly to position $102_{P3}$, corresponding to the second position ($2_{P2}$) in the four-exposure procedure, it will be seen that the same two holes 132a and 132b of collimator 130 will receive radiation, but the mid-way hole 132ab will not. However, in this nine-exposure procedure of FIG. 7, the radiation source is moved to the mid-way position $102_{P2}$, whereupon the mid-way hole 132ab will receive radiation, but the other two holes 132a and 132b will not. After the exposure in position $102_{P2}$, the radiation source is moved to position $102_{P3}$, then to the mid-way (along the Y-axis) position $102_{P4}$ and successively to the other positions until it reaches the ninth position 102p9 to complete the nine-exposure procedure.

It will thus be seen that during each of the nine exposures, the radiation will pass through some of the post-body collimator holes 132 to the underlying element of the detector, but no direct radiation will pass through others of the holes 132. Accordingly, any reading obtained from the elements of the detector underlying the holes not receiving direct radiation will be attributed to scatter or other extraneous noise. The described nine-exposure procedure illustrated in FIG. 7 can thus be used for measuring the level of scatter or other extraneous noise involved in the measurement of the useful information (i.e. the detected direct radiation levels), which measured scatter or noise can be used by the data processor for reducing their effects on the final, reconstructed image.

It will thus be seen that the nine-exposure procedure has the additional advantage, over the above-described four-exposure procedure, of not only increasing the enhancement of the resolution from about a factor of two to about a factor of three, but also of reducing the effects of scatter and other extraneous noise. An additional advantage of the nine-exposure procedure is that the holes in the post-body collimator 130 can be made much coarser than in the pre-body collimator 120, thereby simplifying the manufacture of such collimators and also their alignment.

In both described embodiments, the plurality of exposures would be made after the point-source (2 or 102) has been displaced to the required position as described above. This can be effected, e.g. by pulsing the point source after the displacement has been completed, or by using a chopper which blocks the radiation from the object until the displacement has been completed. As also indicated earlier, the actual displacement of the point source can be effected via the drive 40 in FIG. 1 either by moving the X-ray tube itself, or by deflecting the electron beam within the X-ray tube to cause it to impinge on different portions of the tube target. In the four-exposure procedure, the displacement can be done by tracing a circle, rather than a square, with the exposures being made at the four corner points defining the square. Further, instead of displacing the radiation source with respect to the collimators, the radiation source may be fixed and the collimators displaced with respect thereto.

The main function of the post-body collimator (30 or 130) is to reduce the effects of scatter. Accordingly, in some applications it may be omitted, or its holes may be of substantially larger size than described above, thereby simplifying manufacturing and alignment problems. The radiation-sensitive surface receiving the radiations passing through the examined body is preferably in the form of a single scintillation crystal detector, but may be in the form of other radiation-sensitive detectors. Many other variations, modifications and applications of the invention will be apparent.

What is claimed is:

1. A method of examining a body by means of penetrating radiation projected through the body onto a two-dimensional radiation-sensitive surface to produce a two-dimensional pattern of the radiation absorbed by the body; characterized in:

disposing, between the body and the source of said radiation, a pre-body collimator having a two-dimensional array of radiation-transmitting holes each bordered by radiation non-transmitting walls;

effecting a plurality of successive exposures of said body by projecting said radiation through said collimator and said body during a plurality of successive exposure periods in each of which the radiation source is at a different location with respect to the collimator, such that during the successive exposures, the radiation from the source impinging on the same elements of the radiation-sensitive surface passes along different ray paths defined by the holes in the collimator;

detecting and storing the radiation level received by said radiation-sensitive surface elements during each of said exposure periods;

and processing said stored radiation levels to reconstruct said two-dimensional radiation pattern with enhanced resolution.

2. The method according to claim 1, wherein said radiation source is displaced with respect to said collimator to the different locations for effecting the plurality of successive exposures of said body.

3. The method according to claim 1, wherein a post-body collimator is disposed between the body and the radiation-sensitive surface in fixed relationship to said prebody collimator and also has a two-dimensional array of radiation-transmitting holes each bordered by a radiation non-transmitting wall so dimensioned and arrayed with respect to those of said pre-body collimator such that the radiations passing through the same hole in the post-body collimator to the underlying radiation-sensitive surface element during the successive exposures pass through different holes in the prebody collimator during said successive exposures.

4. The method according to claim 1, wherein said radiation source is located at a plurality of different relative positions with respect to said pre-body collimator along both orthogonal axes during the successive exposures.

5. The method according to claim 4, wherein four successive exposures are effected, said radiation source being located at two different positions with respect to said pre-body collimator along each orthogonal axis during the four exposures, such that each radiation-sensitive element in the four exposures receives the radiation passing along four contiguous ray paths through the body.

6. The method according to claim 4, wherein nine successive exposure periods are effected, said radiation source being located at three different positions with respect to said pre-body collimator along each orthogonal axis during the nine exposures.

7. The method according to claim 1, wherein said penetrating radiation is X-rays.

8. The method according to claim 7, wherein said radiation source is located at a different location with respect to the collimator during each of said plurality of exposures by deflecting the electronic beam of an X-ray tube across the target of the X-ray tube.

9. The method according to claim 7, wherein said radiation source is located at a different location with respect to the collimator during each of said plurality of exposures by displacing the X-ray tube with respect to the collimator.

10. The method according to claim 7, wherein said radiation source is located at a different location with respect to the collimator during each of said plurality of exposures by displacing the collimator with respect to said X-ray source.

11. The method according to claim 1, wherein said radiation-sensitive surface is constituted of a scintillating detector optically coupled to an image intensifier forming an image on a vidicon photoconductive surface, which image is scanned by an electron beam to detect and store the radiation level received by each element of said scintillating detector.

12. The method according to claim 11, wherein the output of said vidicon is fed to an analog-to-digital converter whose output is processed in a digital processor to reconstruct said two-dimensional radiation pattern.

13. The method according to claim 12, wherein the output of said digital processor is displayed on a display terminal.

14. Apparatus for examining a body by means of penetrating radiation projected through the body onto a two-dimensional radiation-sensitive surface to produce a two-dimensional pattern of the radiation absorbed by said body, characterized in that said apparatus includes:
a pre-body collimator disposed between the body and the source of said radiation, said collimator having a two-dimensional array of radiation-transmitting holes each bordered by radiation non-transmitting walls;
displacing means for effecting relative displacement between said radiation source and said collimator;
control means for controlling said radiation source to cause same to effect a plurality of successive exposures of said body by projecting said radiation through said body during a plurality of successive exposure periods in each of which the radiation source is at a different location with respect to said collimator such that during the successive exposures, the radiation from the source impinging on the same elements of the radiation-sensitive surface passes along different ray paths defined by different holes in the collimator;
detector means for detecting the radiation level received by each of said radiation-sensitive surface elements during each of said exposure periods;
storing means for storing said detected radiation levels;
and data processor means for processing said stored radiation levels to reconstruct said two-dimensional radiation pattern but with enhanced resolution.

15. Apparatus according to claim 14, further including a post-body collimator disposed between the body and the radiation-sensitive surface in fixed relationship to said pre-body collimator, said post-body collimator also having a two-dimensional array of radiation-transmitting holes each bordered by a radiation non-transmitting wall so dimensioned and arrayed with respect to said pre-body collimator such that the radiations passing through the same hole in the post-body collimator to the underlying radiation-sensitive surface element during the successive exposures pass through different adjacent holes in the pre-body collimator during said successive exposures.

16. Apparatus according to claim 14, wherein said control means includes displacing means for effecting relative displacement between said radiation source and said collimator to a plurality of different relative positions along both orthogonal axes during the successive exposure periods.

17. Apparatus according to claim 16, wherein said displacing means displaces said radiation source to two different locations along each orthogonal axis during the successive exposure periods, such that each radiation-sensitive element receives the radiation passing along four different ray paths through the body.

18. Apparatus according to claim 16, wherein said displacing means displaces said radiation source to three different locations along each orthogonal axis during the successive exposure periods.

19. Apparatus according to claim 14, wherein said radiation source is an X-ray tube.

20. Apparatus according to claim 19, wherein said displacing means displaces said radiation source to different locations by deflecting the electronic beam of the X-ray tube across the target of the X-ray tube.

21. Apparatus according to claim 19, wherein said displacing means displaces said X-ray tube to different locations.

22. Apparatus according to claim 14, wherein said radiation-sensitive surface is constituted of a scintillating detector optically coupled to an image intensifier forming an image on a vidicon photoconductive surface, which image is scanned by an electron beam to detect and store the radiation levels received by each element of said scintillation detector.

23. Apparatus according to claim 22, further including an analog-to-digital converter, and a digital processor, the output of said vidicon being fed to said analog-to-digital converter whose output is processed in said digital processor to reconstruct said two-dimensional radiation pattern.

24. Apparatus according to claim 23, further including a display terminal for displaying the output of said digital processor.

* * * * *